United States Patent [19]

Stockel et al.

[11] Patent Number: 4,617,189

[45] Date of Patent: Oct. 14, 1986

[54] USE OF SELENIUM-CONTAINING COMPOUNDS FOR NEGATING THE TOXIC EFFECTS OF PLATINUM COMPOUNDS USED IN CHEMOTHERAPY, AND A NOVEL SELENIUM-CONTAINING PLATINUM COMPOUND AND USE THEREOF AS AN ANTI-CANCER MEDICINE

[76] Inventors: Richard F. Stockel, 475 Rolling Hills Rd., Bridgewater, N.J. 08807; Philip E. Dumas, 137 Louise Dr., Morrisville, Pa. 19067

[21] Appl. No.: 737,130

[22] Filed: May 23, 1985

Related U.S. Application Data

[60] Division of Ser. No. 484,874, Apr. 14, 1983, Pat. No. 4,556,571, which is a continuation-in-part of Ser. No. 312,300, Jan. 16, 1984, abandoned.

[51] Int. Cl.$^4$ ............................................. A61K 33/04
[52] U.S. Cl. ......................................................... 424/162
[58] Field of Search ........................................ 424/162

[56] References Cited

U.S. PATENT DOCUMENTS

| | | | |
|---|---|---|---|
| 3,892,790 | 7/1975 | Tobe et al. | 260/429 |
| 4,080,324 | 3/1978 | Hoeschele | 544/225 |
| 4,115,418 | 9/1978 | Gale et al. | 260/429 |
| 4,119,653 | 10/1978 | Tobe et al. | 260/429 |
| 4,119,654 | 10/1978 | Tobe et al. | 260/429 |
| 4,137,248 | 1/1979 | Gale et al. | 260/429 |
| 4,140,707 | 2/1979 | Cleare et al. | 260/429 |
| 4,151,185 | 4/1979 | Allcock et al. | 260/429 |
| 4,163,839 | 8/1979 | Umezawa et al. | 536/24 |
| 4,182,724 | 1/1980 | Tobe et al. | |
| 4,203,912 | 5/1980 | Hydes et al. | 260/429 |
| 4,340,590 | 7/1982 | Levitt | 424/162 |
| 4,512,977 | 4/1985 | Lundy | 424/162 |

OTHER PUBLICATIONS

Merck Index, 1976 (9th Ed), pp. 1091–1092.

*Primary Examiner*—Stanley J. Friedman
*Attorney, Agent, or Firm*—Armstrong, Nikaido, Marmelstein & Kubovcik

[57] ABSTRACT

The toxic effects of platinum compounds used in chemotherapy can be negated by the use of a selenium-containing compound. A new selenium-containing platinum compound has been found to be useful as a so-called platinum compound type anti-cancer medicine which can self-detoxify platinum toxicity.

2 Claims, No Drawings

USE OF SELENIUM-CONTAINING COMPOUNDS FOR NEGATING THE TOXIC EFFECTS OF PLATINUM COMPOUNDS USED IN CHEMOTHERAPY, AND A NOVEL SELENIUM-CONTAINING PLATINUM COMPOUND AND USE THEREOF AS AN ANTI-CANCER MEDICINE

This is a division of Ser. No. 484,874 (4/14/83), now U.S. Pat. No. 4,556,571, which is a C-I-P of Ser. No. 312,300 (1/016/84), now abandoned.

The present invention relates to a method of negating the toxic effects of platinum compounds. More particularly, the present invention relates to a method of negating the toxic effects of platinum compounds used in chemotherapy, which method comprises administering to a patient a selenium-containing compound. The present invention is also concerned with a novel selenium-containing platinum compound which can be effectively used as a so-called platinum compound type anti-cancer medicine which can self-detoxify platinum toxicity.

It is well known that platinum complexes are used in cancer chemotherapy. Rosenberg et al "Nature", 222, 385-386 (1969) have, for the first time, shown that a group of platinum coordination complexes possesses anti-tumor activity in experimental animal tumors. Cis-diaminedichloroplatinum II (hereinafter referred to as "Cisplatin") which is one of the platinum coordination complexes constituting the above group that was introduced into clinical trials by the National Cancer Institute in 1972. Cisplatin is currently used to treat a wide range of tumor types common to humans.

Cisplatin is a water-soluble square planar coordination complex containing a central platinum atom surrounded by two chloride atoms and two ammonia moieties. Since a prime mechanism of inhibition of tumor growth by Cisplatin appears to be inhibition of DNA synthesis, it has been suggested that the cis configuration of Cisplatin favors the formation of intrastrand crosslinks in DNA. Since the discovery of this platinum complex, the patent literature is replete with other analogs and homologs of Cisplatin. U.S. Pat. No. 3,892,790 discloses a number of square planar platinum complexes with nitrogen atoms coordinated to the platinum where the nitrogen is part of an alicyclic monofunctional or difunctional amine. U.S. Pat. No. 4,119,653 describes a complex where the amine is a phenylene diamine. U.S. Pat. No. 4,115,418 describes a complex where the nitrogen atoms are a part of 1,2-diaminocyclohexane. U.S. Pat. Nos. 4,119,653 and 4,119,654 describe platinum complexes that have six sites of coordination where the apex sites are hydroxy groups. U.S. Pat. No. 4,137,248 describes a platinum complex of 4-carboxyphthalato (1,2-diaminocyclohexane)-platinum II and alkali metal salts thereof. U.S. Pat. No. 4,140,707 describes malonato platinum coordinated compounds and a method of treating malignant tumors comprising the parenteral administration thereof. Still another novel composition is described in U.S. Pat. No. 4,151,185 where a complex or salt of a platinum (II) compound is bonded to a nitrogen containing polymer. U.S. Pat. No. 4,182,724 is similar in nature to U.S. Pat. Nos. 4,119,653 and 4,119,654. U.S. Pat. No. 4,203,912 teaches that effective platinum anti-tumor complexes can be prepared when the cis ligands are sulfate, phosphate, nitrate, tartronate, rather than chloride. Yet another U.S. Pat. No. 4,206,208 describes the use of 4-carboxyphthalato (1,2-diaminocyclohexane)platinum (II) and alkali metal salts thereof with cyclophosphamide and 5-fluorouracil as combination drugs in the treatment of leukemia.

Despite the potent anti-tumor properties of platinum compounds as described above, their use has been restricted due to the toxicity of the platinum.

These toxic effects of platinum compounds have been observed and studied in mice, dogs, monkeys and in human patients who have undergone platinum chemotherapy. It is known that renal kidney damage, bone marrow depletion, degeneration of intestinal mucosa and the like are the result of the toxic effects of the platinum. For information concerning toxic effects of platinum compounds, reference may be made to several chapters in the textbook, *Cisplatin*, published by Academic Press, Inc., N.Y., 1981, which deal with the associated problems of toxicity during the administration of these platinum compounds for cancer treatment. As describd above, due to the toxic effects of platinum compounds, the use of platinum compounds having the potent anti-tumor properties has been restricted and, therefore, any compound that would negate these toxic effects of the platinum would greatly enhance the chemotherapeutic treatment of cancer in tumors where these platinum compounds are utilized.

The present inventors have made extensive and intensive studies in order to obtain a medicine excellent in detoxification effect against the platinum toxicity. As a result, the present inventors have found that selenium-containing compounds have excellent effects of detoxification against the platinum toxicity. Further, the present inventors have made extensive and intentive studies with a view to obtaining a so-called platinum compound type anti-cancer medicine possessing a self-detoxification effect against the platinum toxicity but not sacrificing the anti-cancer properties. As a result, the present inventors have found that a new selenium-containing platinum compound of the later-mentioned formula (1) can be effectively used as a so-called platinum compound type anti-cancer medicine which can self-detoxify platinum toxicity. The present invention has been completed based on the above.

With respect to selenium, it is known that selenium has protective effects against several heavy metals in numerous biological systems ("Biochemical Effects of Environmental Pollutants", Chapter 21, entitled "Metabolic Interactions of Selenium with Heavy Metals" by R. A. Rimerman, D. R. Buhler and P. D. Whanger).

Although the mechanism in which selenium negates heavy metal toxicity is unknown, there are many studies which indicate or suggest possible mechanisms. As the mechanisms suggested in these studies, there can be mentioned selenium-metal binding, selenium-metal or selenium-metal protein aggregation, enhancement of immune response by selenium, tissue/or subcellular redistribution of metal by selenium, selenium induced shift of metal among soluble cytosol proteins, selenium requirement in metal excretion and enhanced or reduced metabolism of metal, for example, in the demethylation of methyl mercury cation. Protection of selenium against cadmium toxicity was first shown by Kar and co-workers in 1969, who observed that selenium prevents cadmium induced testicular damage. Protection against the toxicity of other metals including mercury, silver and thallium have been subsequently observed by other researchers. However, the mechanisms of detoxification of the above-mentioned heavy metals by selenium are complex and are not identical for all metals or all forms of the same metal. Mechanisms may involve a direct binding between selenium and the heavy metal; a direct binding between selenium metal, and other small molecules or macro-molecules; or an indirect stoichiometric or catalytic effect of selenium mediated by other molecules, such as an enzyme. The affinity of mercury, methyl mercury and cadmium for sulfhydryl groups which are groups containing sulfur is very strong, but the affinity of these metals for selenium is much greater. Namely, the affinity of selenium for metals is much greater than that of metals for groups containing sulfur. In addition, selenium can replace the sulfur in the sulfhydryl groups in many organs of the body. Detoxification may involve redistribution of the metal among tissues, subcellular fractions or molecules of the same function.

The only information pertaining to detoxification of platinum due to chemotherapeutic treatment with platinum compounds involves the use of chelating agents such as sodium diethyldithiocarbamate. The work related to the use of sodium diethyldithiocarbamate was reported by Richard F. Borch et al in the proceedings of the National Academy of Science, Volume 76, number 12, pages 6611–6614, December, 1979 and in the same journal, Volume 77, number 9, page 5440–5444, September, 1980. In these studies, the nephrotoxic effects of Cisplatin in female rats were effectively inhibited by administration of sodium diethyldithiocarbamate in doses of 750 mg/kg intraperitoneally or 100 mg/kg intravenously two hours after the administration of the sulfur compound.

As apparent from the above, although it was known that selenium had a protective effect or a detoxification effect against the toxicity of several specific metals, it was not known at all that selenium had a detoxification effect on platinum toxicity. Sodium diethyldithiocarbamate was also recognized as having a detoxification effect against platinum toxicity. However, the sulfur compound, namely, sodium diethyldithiocarbamate has been considered to be strongly bonded to platinum to negate the platinum toxicity, but, as described before, selenium is believed to be bonded to metals, for example platinum, more strongly than the groups containing sulfur are bonded. In other words, it is believed that selenium is bonded to platinum more strongly than the sulfur compound is bonded, thereby to form a stable complex so that the platinum toxicity is negated.

It is, accordingly, an object of the present invention to provide a method of negating the toxic effects of platinum compounds used in chemotherapy, which comprises administering to a patient a selenium-containing compound.

Another object of the present invention is to provide a novel selenium-containing platinum compound which can be effectively used as a so-called platinum compound type anti-cancer medicine which can self-detoxify platinum toxicity.

The foregoing and other objects, features and advantages of the present invention will be apparent from the following detailed description.

In one aspect of the present invention, there can be provided a method of negating the toxic effects of platinum compounds which comprises administering to a patient an effective amount of a selenium-containing compound adapted to negate the toxic effects of platinum compounds used in chemotherapy.

As the selenium-containing compounds to be used in the present invention, there can be mentioned a metal salt of selenious acid, a metal salt of selenic acid, an amino acid containing selenium, a selenium yeast and a protein containing selenium. These selenium-containing compounds are effective for negating the toxic effects of platinum remaining in the kidney, liver or other organs in the body after the cancer chemotherapeutic treatment by Cisplatin or other platinum compounds.

As the metal salt of selenious acid to be used in the present invention, there can be mentioned sodium selenite. As the metal salt of selenic acid, there can be mentioned sodium selenate. As the amino acid containing selenium to be used in the present invention, there can be mentioned amino acids containing selenium which has replaced sulfur in the thio or disulfide groups of sulfur-containing amino acids such as selenoamino acids. Specific examples of the selenoamino acids include selenomethionine, selenocysteine, Se-methylselenocysteine, selenocystine, selenohomomethionine and selenohomocystine. As the protein containing selenium, there can be mentioned proteins containing selenium which has replaced sulfur in the thio or disulfide groups or sulfur-containing amino acids. The above mentioned selenium-containing compounds are known and can be purchased from commercial sources or can be prepared easily. For example, sodium selenite, sodium selenate and selenium yeast can be purchased from commercial sources and used without further refinement. Selenocystine and selenohomocystine, examples of the amino acid containing selenium, can be prepared according to E. P. Painter, J. Amer. Chem. Soc., 69, 229(1947) and J. Amer. Chem. Soc., 69, 232(1947) respectively. These selenium-containing compounds have shown that they are effective protective agents against platinum toxicity.

The selenium-containing compounds to be used in the present invention also include amines containing selenium such as $\beta$-seleno ethylamine, 2-phenylseleno-1,3-diaminopropane, 4-phenylselenomethylene-1,2-diaminobenzene, 2-seleno-1,3-diaminopropane and 4-phenylselenosemicarbazide; seleno carbohydrates such as 1-$\beta$-D-seleno-2,3,4,6-tetra-O-acetyl-D-glucopyranose, selenoglucopyranose, 1-$\beta$-D-seleno-2,3,4,6-tetra-O-acetyl-D-galactopyranose, 1-$\beta$-D-selenogalactopyranose, 1-$\alpha$-D-seleno-2,3,4,6-tetra-O-acetyl-D-mannopyranose and 1-$\alpha$-D-selenomannopyranose; and seleno heterocyclic bases such as 6-selenoguanine, 6-selenoguanosine, 5-selenocytosine, 5-selenocytidine, 6-selenopurine, 6-selenopurineriboside, 8-selenoguanine, 8-selenoguanosine, 8-selenoadenine and 8-selenoadenosine.

The selenium-containing compunds to be used in the present invention can be administered orally or parenterally, for example, in the form of an intravenous injection, a hypodermical injection or a suppository. The dosage may vary depending upon ages, severities and body weights of patients, but a selenium-containing compound as an active ingredient may be usually administered in a dialy dose of from about 0.6 to about 300 mg for adults, if necessary, in divided dosage forms. The selenium-containing compounds can be used concomitant with the chemotherapeutic treatment of cancer by platinum complexes or alternatively the selenium-containing compounds can be administered prior to treatment with the platinum complexes to build up levels of selenium in the body that will mitigate the toxic side effects of the platinum complexes. Even though selenium itself at high levels in the body can be toxic, the body can tolerate low levels and can detoxify platinum poisoning particularly in the renal system and liver, where platinum concentrates after chemotherapeutic treatment with platinum complexes.

In the present invention, the selenium-containing compound as such may be administered. However, a pharmaceutical composition which comprises a selenium-containing compound as an active ingredient is usually administered. The composition or preparation may be of the form of, for example, capsule, granule, powder, tablet, pill, ointment, syrup, injection, suppository or the like. As the pharmaceutical agents to be used in the pharmaceutical composition, there can be mentioned excipients such as white sugar, lactose, glucose, starch, corn starch, mannite, sorbite, cellulose, talc, cyclodextrin and the like; binding agents such as cellulose, methylcellulose, hydroxypropylcellulose, hydroxypropylmethylcellulose, polyvinyl pyrrolidone, gelatin, gum arabic, polyethylene glycol, white sugar, starch and the like; disintegrators such as starch, carboxymethylcellulose, calcium salts of carboxymethylcellulose and the like; lubricants such as talc and the like; preservatives such as sodium benzoate, sodium bisulfite and the like; suspending agents such as methylcellulose, aluminum stearate, magnesium stearate and the like; and bases such as polyethylene glycol, Witepsol, white petrolatum and the like. According to the kinds of forms of the pharmaceutical composition, appropriate pharmaceutical agents are used. Examples of the pharmaceutical compositions are given as follows.

Composition 1

Sodium selenite: 6.3 mg
lactose: 20.3 mg
corn starch: 7.0 mg
hydroxypropylcellulose: 1.4 mg
carboxymethylcellulose calcium: 1.1 mg
magnesium stearate: 0.2 mg Composition 2 sodium selenate: 6.3 mg
hydroxypropylmethylcellulose: 8.0 mg
crystalline cellulose: 76.0 mg
carboxymethylcellulose calcium: 64.0 mg
magnesium stearate: 4.0 mg Composition 3 selenomethionine: 4.0 mg
lactose: 178.0 mg
corn starch: 37.0 mg
talc: 5.0 mg

The platinum toxicity negating effect of the selenium-containing compounds was affirmed by the determination of blood urea nitrogen (hereinafter often referred to as "BUN") using $BDF_1$ mice. BUN of the mice which have been administered a platinum complex increases due to the platinum poisoning in the kidney. The increase in BUN of mice was suppressed by the administration of the selenium-containing compounds and the platinum toxicity negating effect of the present invention was affirmed. It is desirable to administer selenium compounds concomitant with the administration of Cisplatin or alternatively prior to the administration of Cisplatin. The method of negating platinum toxicity of the present invention will be illustrated in more detail by way of Examples later.

In another aspect of the present invention, there is provided a novel selenium-containing platinum compound which can be effectively used as a so-called platinum compound type anti-cancer medicine which can self-detoxify platinum toxicity, and which has the following general formula:

 (1)

wherein

R and R' each independently stand for
  a selenoalkylmonoamine,
  a selenoamino acid having one amine group,
  an unsubstituted or substituted selenoglucose radical,
  an unsubstituted or substituted selenogalactose radical, or
  an unsubstituted or substituted selenomannose radical; or R and R' together stand for
  a selenoalkyldiamine,
  a selenoaralkyldiamine,
  a selenoamino acid having two amino groups,
  a selenonucleic acid base radical,
  a selenoribosylnucleic acid base radical, or
  an unsubstituted or substituted selenosemicarbazide; and X and X' each independently stand for Cl, $NO_2$, or $NO_3$, or X and X' together stand for $>SO_3$, $>SO_4$ or

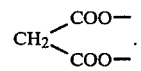

As the selenoalkylmonoamine in the formula (1), there can be mentioned those represented by the formula $R_1Se(CH_2)_nNH_2$ (wherein $R_1$ stands for H, an alkyl group having 1 to 6 carbon atoms or a phenyl group, and n is an integer of 1 to 6). Those represented by $R_1Se(CH_2)_2NH_2$ ($R_1$ is as defined above) are especially preferable. In the selenium-containing platinum compound represented by the formula (1) in which R and R' each independently stand for a selenoalkylmonoamine as mentioned above, the nitrogen atom of the selenoalkylmonoamine is coordinately bonded to the platinum atom.

As the selenoamino acid having one amino group in the formula (1), there can be mentioned selenomethionine, selenohomomethionine, selenocysteine and Se-methylselenocysteine. In the selenium-containing platinum compound represented by the formula (1) in which R and R' each independently stand for a selenoamino acid having one amino group, the nitrogen atom of the selenoamino acid is coordinately bonded to the platinum atom.

The unsubstituted or substituted selenoglucose radical in the above formula (1) is represented by the following general formula:

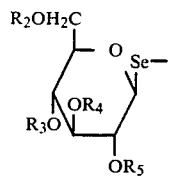
(2)

(wherein $R_2$, $R_3$, $R_4$ and $R_5$ each independently stand for H, an acetyl group, a propionyl group or a butyryl group). In the above formula (2), it is preferable that $R_2$, $R_3$, $R_4$ and $R_5$ each independently stand for H or an acetyl group. In the selenium-containing platinum compound represented by the formula (1) in which R and R' each independently stand for an unsubstituted or substituted selenoglucose radical, the selenium atom of said selenoglucose radical is directly bonded to the platinum atom. Specific examples of the selenium-containing platinum compound represented by the formula (1) in which R and R' each independently stand for an unsubstituted or substituted selenoglucose radical of the formula (2) include di-(1-β-D-glucopyranosylseleno)dichloroplatinum and di-(2,3,4,6-tetra-O-acetyl-1-β-D-glucopyranosylseleno)dichloroplatinum. The former is given when $R_2$, $R_3$, $R_4$ and $R_5$ in the formula (2) each stand for H, that is, R and R' in the formula (1) each stand for a 1-β-D-glucopyranosylseleno radical, and X and X' in the formula (1) each stand for Cl. While, the latter is given when $R_2$, $R_3$, $R_4$ and $R_5$ in the formula (2) each stand for an acetyl group, that is, R and R' in the formula (1) each stand for a 2,3,4,6-tetra-O-acetyl-1-β-D-glucopyranosylseleno radical, and X and X' in the formula (1) each stand for Cl.

The unsubstituted or substituted selenogalactose radical in the formula (1) is represented by the following general formula:

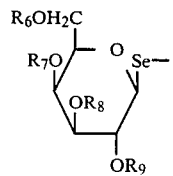
(3)

(wherein $R_6$, $R_7$, $R_8$ and $R_9$ each independently stand for H, an acetyl group, a propionyl group or a butyryl group). In the above formula (3), it is preferable that $R_6$, $R_7$, $R_8$ and $R_9$ each independently stand for H or an acetyl group. In the selenium-containing platinum compound represented by the formula (1) in which R and R' each independently stand for an unsubstituted or substituted selenogalactose radical, the selenium atom of said selenogalactose radical is directly bonded to the platinum atom. Specific examples of the selenium-containing platinum compound represented by the formula (1) in which R and R' each independently stand for an unsubstituted or substituted selenogalactose radical include di-(1-β-D-galactopyranosylseleno)dichloroplatinum and di-(2,3,4,6-tetra-O-acetyl-1-β-D-galactopyranosylseleno)dichloroplatinum. The former is given when $R_6$, $R_7$, $R_8$ and $R_9$ in the formula (3) each stand for H, that is, R and R' in the formula (1) each stand for a 1-β-D-galactopyranosylseleno radical, and X and X' in the formula (1) each stand for Cl. While, the latter is given when $R_6$, $R_7$, $R_8$ and $R_9$ in the formula (3) each stand for an acetyl group, that is, R and R' in the formula (1) each stand for a 2,3,4,6-tetra-O-acetyl-1-β-D-galactopyranosylseleno radical, and X and X' in the formula (1) each stand for Cl.

The unsubstituted or substituted selenomannose radical in the above formula (1) is represented by the following general formula:

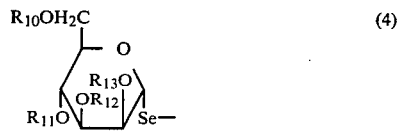
(4)

(wherein $R_{10}$, $R_{11}$, $R_{12}$ and $R_{13}$ each independently stand for H, an acetyl group, a propionyl group or a butyryl group). In the above formula (4), it is preferable that $R_{10}$, $R_{11}$, $R_{12}$ and $R_{13}$ each independently stand for H or an acetyl group. In the selenium-containing platinum compound represented by the formula (1) in which R and R' each independently stand for an unsubstituted or substituted selenomannose radical, the selenium atom of said selenomannose radical is directly bonded to the platinum atom. Specific examples of the selenium-containing platinum compound represented by the formula (1) in which R and R' each independently stand for an unsubstituted or substituted selenomannose radical of the formula (4) include di-(1-α-D-mannopyranosylseleno)dichloroplatinum and di-(2,3,4,6-tetra-O-acetyl-1-α-D-mannopyranosylseleno)dichloroplatinum. The former is given when X and X' in the formula (1) each stand for Cl and $R_{10}$, $R_{11}$, $R_{12}$ and $R_{13}$ in the formula (4) each stand for H, that is, R and R' in the formula (1) each stand for a 1-α-D-mannopyranosylseleno radical. While, the latter is given when X and X' in the formula (1) each stand for Cl and $R_{10}$, $R_{11}$, $R_{12}$ and $R_{13}$ in the formula (4) each stand for an acetyl group, that is, R and R' in the formula (1) each stand for a 2,3,4,6-tetra-O-acetyl-1-α-D-mannopyranosylseleno radical.

As examples of the selenoalkyldiamine in the formula (1), there can be mentioned

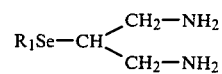

wherein $R_1$ stands for H, an alkyl group having 1 to 6 carbon atoms or a phenyl group). In the selenium-containing platinum compound represented by the formula (1) in which R and R' together stand for a selenoalkyl diamine, the two nitrogen atoms of said selenoalkyldiamine each are coordinately bonded to the platinum atom.

As the selenoaralkyldiamine in the formula (1), there can be mentioned those represented by the general formula

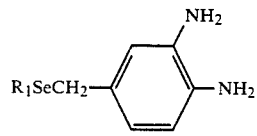

(wherein $R_1$ stands for H, an alkyl group having 1 to 6 carbon atoms or a phenyl group). In the selenium-containing platinum compound represented by the formula (1) in which R and R' together stand for a selenoaralkyl-diamine, the two nitrogen atoms of said selenoaralkyldiamine each are coordinately bonded to the platinum atom.

As the selenoamino acid having two amino groups in the formula (1), there can be mentioned selenocystine and selenohomocystine. In the selenium-containing platinum compound represented by the formula (1) in which R and R' together stand for a selenoamino acid having two amino groups, the two nitrogen atoms of said selenocystine each are coordinately bonded to the platinum atom.

The selenonucleic acid base radical (radical N) and selenoribosylnucleic acid base radical (radical R) in the formula (1) are represented by the following general formula:

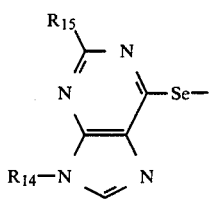

(wherein $R_{14}$ represents H for the radical N or a 1-$\beta$-D-ribofuranosyl group for the radical R and $R_{15}$ stands for H or an amino group);

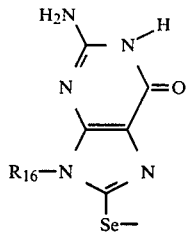

(wherein $R_{16}$ represents H for the radical N or a 1-$\beta$-D-ribofuranosyl group for the radical R);

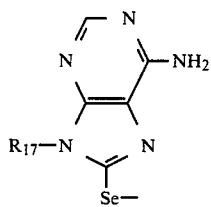

(wherein $R_{17}$ represents H for the radical N or a 1-$\beta$-D-ribofuranosyl group for the radical R); or

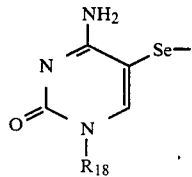

(wherein $R_{18}$ represents H for the radical N or a 1-$\beta$-D-ribofuranosyl group for the radical R).

The above selenonucleic acid base radical and selenoribosylnucleic acid base radical may be unsubstituted or substituted. In the selenium-containing platinum compound represented by the formula (1) in which R and R' together stand for a selenonucleic acid base radical or a selenoribosylnucleic acid base radical represented by the formula (5), (6) or (7), the selenium atom and the nitrogen atom at the 7th position of said selenonucleic acid base radical or selenoribosylnucleic acid base radical each are directly bonded to the platinum atom. While in the selenium-containing platinum compound represented by the formula (1) in which R and R' together stand for a selenonucleic acid base radical or a selenoribosylnucleic acid base radical represented by the formula (8), the selenium atom and the nitrogen atom which is bonded to the carbon atom at the 4th position of said selenonucleic acid base radical or selenoribosylnucleic acid base radical each are directly bonded to the platinum atom. Specific examples of the selenium-containing platinum compound represented by the formula (1) in which R and R' together stand for a selenonucleic acid base radical or a selenoribosylnucleic acid base radical which is represented by any one of the above formulae (5) to (8) include 6-selenopurine dichloroplatinum, 6-selenopurineriboside dichloroplatinum, 6-selenoguanine dichloroplatinum, 6-selenoguanosine dichloroplatinum, 8-selenoguanine dichloroplatinum, 8-selenoguanosine dichloroplatinum, 8-selenoadenine dichloroplatinum, 8-selenoadenosine dichloroplatinum, 5-selenocytosine dichloroplatinum and 5-selenocytidine dichloroplatinum. 6-Selenopurine dichloroplatinum is given when X and X' in the formula (1) each stand for Cl and R and R' in the formula (1) together stand for a 6-selenopurine radical represented by the formula (5) in which $R_{14}$ and $R_{15}$ each stand for H. 6-Selenopurineriboside dichloroplatinum is given when X and X' in the formula (1) each stand for Cl and R and R' in the formula (1) together stand for a 6-selenopurine riboside radical represented by the formula (5) in which $R_{14}$ and $R_{15}$ stand for a 1-$\beta$-D-ribofuranosyl group and H, respectively. 6-Selnoguanine dichloroplatinum is given when X and X' in the formula (1) each stand for Cl and R and R' in the formula (1) together stand for a 6-selenoguaine radical represented by the formula (5) in which $R_{14}$ and $R_{15}$ stand for H and an amino group, respectively. 6-Selenoguanosine dichloroplatinum is given when X and X' in the formula (1) each stand for Cl and R and R' in the formula (1) together stand for a 6-selenoguanosine radical represented by the formula (5) in which $R_{14}$ and $R_{15}$ stand for a 1-$\beta$-D-ribofuranosyl group and an amino group, respectively. 8-Selenoguanine dichloroplatinum is given when X and X' in the formula (1) each stand for Cl and R and R' in the formula (1) together stand for a 8-selenoguanine radical represented by the formula (6) in which $R_{16}$ stands for H. 8-Selenoguanosine dichloroplatinum is given when X and X' in the formula (1) each independently stand for Cl and R and R' in the formula (1) together stand for a 8-selenoguanisone radical represented by the formula (6) in which $R_{16}$ stands for a 1-$\beta$-D-ribofuranosyl group. 8-Selenoadenine dichloroplatinum is given when X and X' in the formula (1) each stand for Cl and R and R' in the formula (1) together stand for a selenoadenine radical represented by the formula (7) in which $R_{17}$ stands for H. 8-Selenoadenosine dichloroplatinum is given when X and X' in the formula (1) each stand for Cl and R and R' in the formula (1) together stand for a selenoadenosine radical represented by the formula (7) in which $R_{17}$ stands for a 1-$\beta$-D-ribofuranosyl group. 5-Selenocytosine dichloroplatinum is given when X and X' in the formula (1) each stand for Cl and R and R' in the formula (1) together stand for a selenocytosine radical represented by the formula (8) in which $R_{18}$ stands for H. 5-Selenocytidine dichloroplatinum is given when X and X' in the formula (1) each stand for Cl and R and R' in the formula (1) together stand for a selenocytidine radical represented by the formula (8) in which $R_{18}$ stands for a 1-β-D-ribofuranosyl group.

The unsubstituted or substituted selenosemicarbazide in the formula (1) is represented by the following general formula:

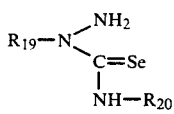
(9)

(wherein $R_{19}$ and $R_{20}$ each independently stand for H, a lower alkyl group or an aryl group). In the selenium-containing platinum compound represented by the formula (1) in which R and R' together stand for an unsubstituted or substituted selenosemicarbazide, the selenium atom and the nitrogen atom at the 1st position of said selenosemicarbazide each are coordinately bonded to the platinum atom. Specific examples of the selenium-containing platinum compound represented by the formula (1) in which R and R' together stand for an unsubstituted or substituted selenosemicarbazide represented by the formula (9) mentioned above include 4-phenylselenosemicarbazide dichloroplatinum. 4-Phenylselenosemicarbazide is given when X and X' in the formula (1) each stand for Cl and R and R' in the formula (1) together stand for 4-phenylselenosemicarbazide represented by the formula (9) in which $R_{19}$ and $R_{20}$ stand for H and a phenyl group, respectively.

The selenium-containing platinum compound of the present invention having the formula (1) as mentioned heretofore is a novel and unknown compound. The method for preparing the selenium-containing platinum compound according to the present invention will be described below.

A selenium-containing platinum compound represented by the formula (1) in which R and R' each independently stand for a selenoalkylmonoamine or R and R' together stand for a selenoalkyldiamine can be obtained as follows. First, a derivative of halogenated alkylmonocarboxylic acid or halogenated alkyldicarboxylic acid is reacted with $R_1SeNa$ (wherein $R_1$ stands for H, an alkyl group having 1 to 6 carbon atoms or a phenyl group) to obtain a derivative of a selenoalkylmonocarboxylic acid or selenoalkyldicarboxylic acid. Then, the obtained derivative of a selenoalkylmonocarboxylic acid or selenoalkyldicarboxylic acid is reacted with ammonia to obtain a selenoalkylmonocarboxylic acid amide or selenoalkyldicarboxylic acid diamide, followed by the reduction of the obtained monoamide or diamide. By the reduction, a selenoalkylmonoamine or selenoalkyldiamine is obtained. Then, the selenoalkylmonoamine or selenoalkyldiamine thus obtained is reacted with potassium tetrachloroplatinate (II) to give a selenoalkylamine dichloroplatinum which is one form of the selenium-containing platinum compound according to the present invention and which has the following formula:

(10)

(wherein $R_{21}$ and $R'_{21}$ each independently stand for a selenoalkylmonoamine, or $R_{21}$ and $R'_{21}$ together stand for a selenoalkyldiamine). The two chlorine atoms in the compound of the formula (10) can each be substituted with a group of $NO_2$ or $NO_2$, or can together be substituted with a group of $>SO_3$, $>SO_4$ or

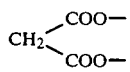

by reacting said compound represented by the formula (10) with a silver, sodium or potassium salt of $NO_2$, $NO_3$, $>SO_3$, $>SO_4$ or

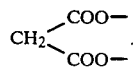

The method of preparing the compound of the formula (10) will now be described in more detail. In reacting a derivative of halogenated alkylmonocarboxylic acid or halogenated alkyldicarboxylic acid with $R_1SeNa$ (wherein $R_1$ is as defined above) to form a derivative of a selenoalkylmonocarboxylic acid or selenoalkyldicarboxylic acid, an amount of the derivative of halogenated alkylmonocarboxylic acid or halogenated alkyldicarboxylic acid may be more than 0.5 equivalent, preferably 0.5 to 3 equivalents to $R_1SeNa$. Reaction temperature is usually room temperature to 120° C., preferably 60° to 100° C. Reaction period of time is usually 0.5 to 24 hours. As the solvent for the above reaction, there may be used an alcohol such as methanol, ethanol, propanol or isopropanol. As the derivative of a halogenated alkylcarboxylic acid, there may be employed a methyl ester, ethyl ester or propyl ester of a halogenated alkylcarboxylic acid. In the next step, the resulting derivative of a selenoalkylmonocarboxylic acid or selenoalkyldicarboxylic acid is reacted with excess ammonia in water at room temperature to 100° C. for 1 to 24 hours to form a selenoalkylmonocarboxylic acid amide or selenoalkyldicarboxylic acid diamide. In reducing the amide thus obtained to form a selenoalkylmonoamine or selenoalkyldiamine, the reduction is conducted, using lithium aluminum hydride and the like, in a solvent such as dioxane, tetrahydrofuran or the like at room temperature to 120° C. for 1 to 24 hours. On the other hand, when $HSeCH_2CH_2NH_2$ as a selenoalkylamine is prepared, $HSeCH_2CH_2NH_2$ can be easily prepared simply by reacting an aqueous ethyleneimine solution with $H_2Se$ at room temperature to 50° C. for several hours to 20 days. An amount of ethyleneimine may be in the range of 1 to 10 equivalents to $H_2Se$. In reacting the selenoalkylmonoamine or selenoalkyldiamine thus obtained with potassium tetrachloroplatinate (II), the selenoalkylmonoamine or selenoalkyldiamine may be employed in an amount of 0.5 to 2 equivalents to potassium tetrachloroplatinate (II). The reaction is carried out in water at room temperature to 80° C. under atmospheric pressure for several hours to 10 days to obtain a selenoalkylamine dichloroplatinum. In the case where the two chlorine atoms in the selenoalkylamine dichloroplatinum thus obtained are substituted with other substituents such as NO₂, NO₃, >SO₃, >SO₄ or

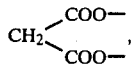

the selenoalkylamine dichloroplatinum is stirred in a hot water (about 50° to 100° C.) with, for example, a silver salt of NO₂, NO₃, >SO₃, >SO₄ or

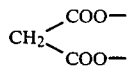

for several hours to 5 days, thereby yielding a selenium-containing platinum compound having a group of NO₂ or NO₃ instead of each of the two chlorine atoms in the formula (10), or a group of >SO₃, >SO₄ or

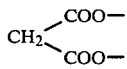

instead of the two chlorine atoms in the formula (10). In this reaction, the selenoalkylamine dichloroplatinum may be employed in an amount of about one equivalent to the salt to be used.

With respect to the preparation of a selenium-containing platinum compound represented by the formula (1) in which R and R' together stand for a selenoaralkyldiamine, an explanation will be given as follows. First, a halogenated aralkyldiamine is reacted with R₁SeNa (wherein R₁ stands for H, an alkyl group having 1 to 6 carbon atoms or a phenyl group) to form a selenoaralkyldiamine. Then, the selenoaralkyldiamine obtained is reacted with potassium tetrachloroplatinate (II) to obtain a selenoaralkyldiamine dichloroplatinum which is one form of the selenium-containing platinum compound of the present invention and which is represented by the following formula:

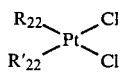

(wherein R₂₂ and R'₂₂ together stand for a selenoaralkyldiamine). The two chlorine atoms in the thus obtained compound of the formula (11) can each be substituted with a group of NO₂ or NO₃, or can together be substituted with a group of >SO₃, >SO₄ or

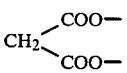

by reacting said compound with silver, sodium or potassium salt of NO₂, NO₃, >SO₃, >SO₄, or

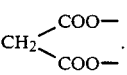

The method of preparing the selenoaralkyldiamine dichloroplatinum of the formula (11) will now be described in more detail. In reacting a halogenated aralkyldiamine with R₁SeNa (wherein R₁ is as defined above) to form a selenoaralkyldiamine, an amount of the halogenated aralkyldiamine may be in the range of 0.5 to 5 equivalents to R₁SeNa. Reaction temperature is usually room temperature to 100° C. Reaction period of time is usually 0.5 to 24 hours. As the solvent for the above reaction, there may be employed an alcohol such as methanol, ethanol, propanol, isopropanol or the like. In reacting the obtained selenoaralkyldiamine with potassium tetrachloroplatinate (II), the selenoaralkyldiamine may be employed in an amount of 0.5 to 2 equivalents to potassium tetrachloroplatinate (II). This reaction is carried in water at room temperature to 80° C. under atmospheric pressure for several hours to 10 days to form a selenoaralkylamine dichloroplatinum. The two chlorine atoms in the obtained selenoaralkylamine dichloroplatinum can be replaced by other substituents such as NO₂, NO₃, >SO₃, >SO₄ and

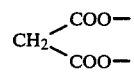

in substantially the same manner as described above with respect to the substitution of the two chlorine atoms of the selenoalkylamine dichloroplatinum represented by the formula (10) with other substituents such as NO₂, NO₃, >SO₃, >SO₄ and

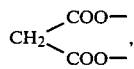

except that a selenoaralkylamine dichloroplatinum is used instead of a selenoalkylamine dichloroplatinum.

A selenium-containing platinum compound of the present invention represented by the formula (1) in which R and R' each independently stand for a selenoamino acid having one amino group, or R and R' together stand for a selenoamino acid having two amino groups can be prepared by reacting a selenoamino acid with potassium tetrachloroplatinate (II) in water under atmospheric pressure while stirring. In this reaction, an amount of a selenoamino acid may be in the range of about 0.5 to 2 equivalents to potassium tetrachloroplatinate (II). Reaction temperature is usually room temperature to 100° C. Reaction period of time is usually several hours to 10 days. By the reaction an intended selenoamino acid dichloroplatinum is obtained. It is known that selenoamino acids are widely present in nature. Herein, commercially available selenoamino acids such as selenomethionine, selenohomomethionine, selenocysteine, Se-methylselenocysteine and the like may be employed. With respect to selenocystine and selenohomocystine, they can be prepared according to E. P. Painter, J. Amer. Chem. Soc., 69, 229(1947) and J. Amer. Chem. Soc., 69, 232(1947), respectively. The two chlorine atoms in the selenoamino acid dichloroplatinum thus obtained can be substituted with other substituents such as NO₂, NO₃, >SO₃, >SO₄ and

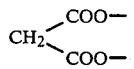

in substantially the same manner as described above with respect to the substitution of the two chlorine atoms of the selenoalkylamine dichloroplatinum represented by the formula(10) with other substituents such as $NO_2$, $NO_3$, $>SO_3$, $>SO_4$ and

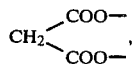

except that a selenoamino acid dichloroplatinum is used instead of a selenoalkylamine dichloroplatinum.

With respect to the production of a selenium-containing platinum compound of the present invention represented by the formula(1) in which R and R' each independently stand for an unsubstituted or substituted selenoglucose radical, an explanation will be given as follows. First, a halogen derivative of acylglucose of the formula:

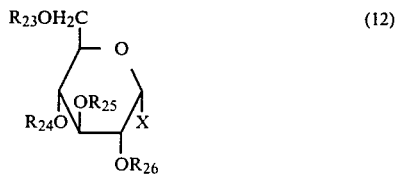

(wherein $R_{23}$, $R_{24}$, $R_{25}$ and $R_{26}$ each independently stand for an acetyl group, a propionyl group or a butyryl group, and X stands for a halogen) is reacted with selenourea according to Wagner, G. and Nuhn, P., Arch. Pharm., 297, 461(1964) to obtain a corresponding derivative of selenoisourea. For example, an acylbromoglucose is reacted with selenourea to form a hydrobromide derivative of acylglucose isoselenourea. The reaction mentioned above is carried out in a ketone as a reaction solvent such as acetone, methylethylketone or the lkie at room temperature to 100° C., generally at the boiling point of the solvent to be employed, for 10 minutes to 5 hours. Selenourea may be employed in an amount of about one equivalent to an acylbromoglucose. The formed selenoisourea derivative is then converted into a derivative of selenoacylglucose according to G. Wagner and P. Nuhn, Z. Chemie., 3, 64(1963) and the derivative of selenoacylglucose thus formed is reacted with potassium tetrachloroplatinate (II) to obtain an acylglucosylseleno platinum compound. For example, an acylglucose selenoisourea hydrobromide is reacted in a mixed solvent of acetone and water containing 0.5 mole of potassium tetrachloroplatinate (II) per mole of the acylglucose selenoisourea hydrobromide and 2 moles of potassium hydroxide per mole of the acylglucose selenoisourea hydrobromide to obtain di-(acylglucosylseleno)dichloroplatinum of the formula:

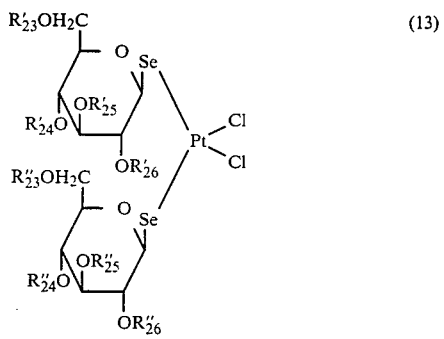

(wherein $R_{23}'$, $R_{24}'$, $R_{25}'$, $R_{26}'$, $R_{23}''$, $R_{24}''$, $R_{25}''$ and $R_{26}''$ each independently stand for an acetyl group, a propionyl group or a butyryl group). The above reaction is usually carried out at 0° C. to room temperature for 10 minutes to 10 hours. The di-(acylglucosylseleno)-dichloroplatinum thus formed can be subjected to deacylation by using excess sodium methoxide, in methanol at room temperature to give di-(glucosylseleno)dichloroplatinum of the formula:

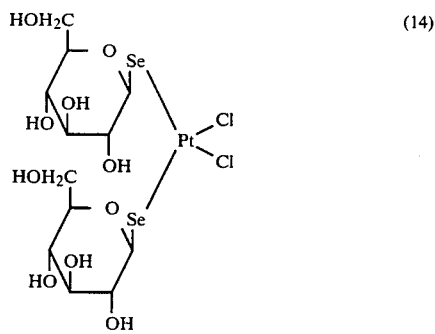

The two chlorine atoms in the selenium-containing platinum compound represented by the formula (13) or (14) thus obtained can be substituted with other substituents such as $NO_2$, $NO_3$, $>SO_3$, $>SO_4$ and

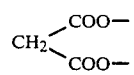

in substantially the same manner as described above with respect to the substitution of the two chlorine atoms of the selenoalkylamine dichloroplatinum represented by the formula(10) with other substituents such as $NO_2$, $NO_3$, $>SO_3$, $>SO_4$ and

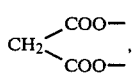

except that a di-(acylglucosylseleno)dichloroplatinum or di-(glucosylseleno)dichloroplatinum is used instead of a selenoalkylamine dichloroplatinum.

A selenium-containing platinum compound of the present invention represented by the formula (1) in which R and R' each independently stand for an unsubstituted or substituted selenogalactose radical can be prepared in substantially the same manner as described above with respect to the production of the compounds represented by the formulae (13) and (14) except that a halogen derivative of acylgalactose of the following formula:

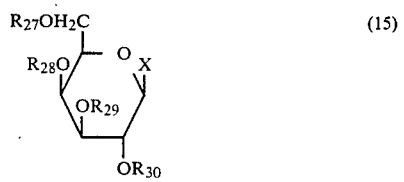

(wherein $R_{27}$, $R_{28}$, $R_{29}$ and $R_{30}$ each independently stand for an acetyl group, a propionyl group or a butyryl group, and X stands for a halogen) is used instead of the halogen derivative of acylglucose of the formula (12), to obtain di-(acylgalactosylseleno)dichloroplatinum of the following formula:

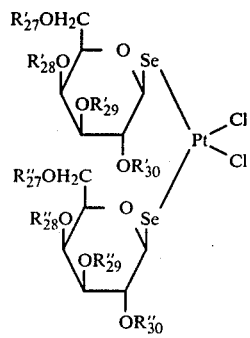
(16)

(wherein $R_{27}'$, $R_{28}'$, $R_{29}'$, $R_{30}'$, $R_{27}''$, $R_{28}''$, $R_{29}''$ and $R_{30}''$ each independently stand for an acetyl group, a propionyl group or a butyryl group) and di-(galactosylseleno)dichloroplatinum of the following formula:

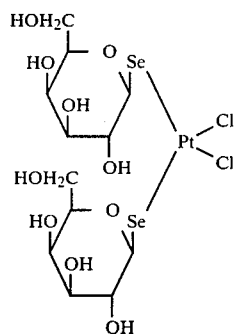
(17)

The two chlorine atoms in the selenium-containing platinum compound represented by the formula (16) or (17) thus obtained can be substituted with other substituents such as $NO_2$, $NO_3$, $>SO_3$, $>SO_4$ and

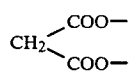

in substantially the same manner as described above with respect to the substitution of the two chlorine atoms of the selenoalkylamine dichloroplatinum represented by the formula (10) with other substituents such as $NO_2$, $NO_3$, $>SO_3$, $>SO_4$ and

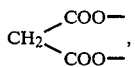, except that a di-(acylgalactosylseleno)dichloroplatinum or di-(galactosylseleno)dichloroplatinum is used instead of a selenoalkylamine dichloroplatinum.

A selenium-containing platinum compound of the present invention represented by the formula (1) in which R and R' each independently stand for an unsubstituted or substituted selenomannose radical can be prepared in substantially the same manner as described with respect to the production of the compounds represented by the formulae (13) and (14) except that a halogen derivative of acylmannose of the following formula:

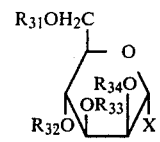
(18)

(wherein $R_{31}$, $R_{32}$, $R_{33}$ and $R_{34}$ each independently stand for an acetyl group, a propionyl group or a butyryl group, and X stands for a halogen) is used instead of the halogen derivative of acylglucose of the formula (12) to obtain di-(acylmannosylseleno)dichloroplatinum of the following formula:

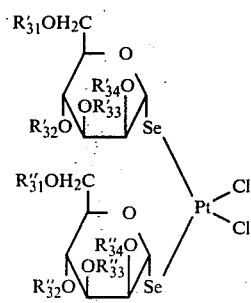
(19)

(wherein $R_{31}'$, $R_{32}'$, $R_{33}'$, $R_{34}'$, $R_{31}''$, $R_{32}''$, $R_{33}''$ and $R_{34}''$ each independently stand for an acetyl group, a propionyl group or a butyryl group) or di-(mannosylseleno)dichloroplatinum of the following formula:

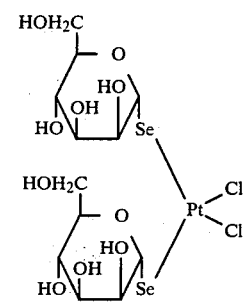
(20)

The two chlorine atoms in the compound of the above formula (19) or (20) can be substituted with other substituents such as $NO_2$, $NO_3$, $>SO_3$, $>SO_4$ and

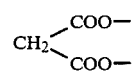

in substantially the same manner as described above with respect to the substitution of the two chlorine atoms of the selenoalkylamine dichloroplatinum represented by the formula(10) with other substituents such as $NO_2$, $NO_3$, $>SO_3$, $>SO_4$ and

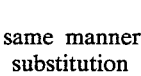, except that a di-(acylmannosylseleno)dichloroplatinum or di-(mannosylseleno)dichloroplatinum is used instead of a selenoalkylamine dichloroplatinum.

A selenium-containing platinum compound of the present invention represented by the formula (1) in which R and R' together stand for a selenonucleic acid base radical or a selenoribosylnucleic acid base radical can be prepared by synthesizing a selenonucleic acid base or selenoribosylnucleic acid base and reacting the obtained selenonucleic acid base or selenoribosylnucleic acid base with potassium tetrachloroplatinate (II). A selenonucleic acid base or selenoribosylnucleic acid base is formed, according to H. G. Mautner et al., J. Am. Chem. Soc., 78, 5292(1956) and J. Med. Chem., 6, 36(1963), by boiling a halogeno nucleic acid base or halogeno ribosylnucleic acid base with selenourea under reflux in absolute ethanol for 0.5 to 5 hours, or alternatively by boiling a halogeno nucleic acid base or halogeno ribosylnucleic acid base with sodium selenide which is obtained from sodium and hydrogen selenide, under reflux in absolute ethanol for 10 to 30 hours. In the above reaction, selenourea or sodium selenide may be employed in an amount substantially equimolar with the halogeno nucleic acid base or halogeno ribosylnucleic acid base to be used. The above-mentioned halogeno nucleic acid base (base N) or halogeno ribosylnucleic acid base (base R) to be used is represented by the following formula:

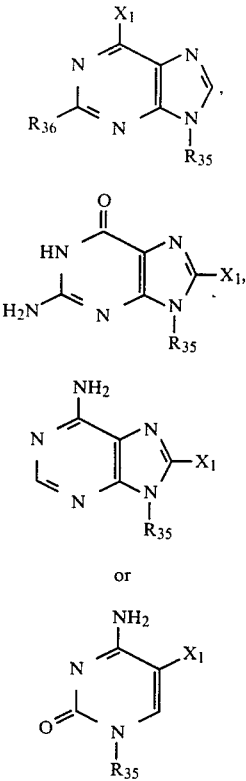

(wherein R$_{35}$ represents H for the base N or a 1-β-D-ribofuranosyl group for the base R, R$_{36}$ stands for H or an amino group and X$_1$ stands for Cl or Br). Specific examples of the halogeno nucleic acid base and halogeno ribosylnucleic acid base include 6-chloro(-bromo)purine, 6-chloro(bromo)purineriboside, 6-chloro(bromo)guanine, 6-chloro(bromo)guanosine, 8-chloro(bromo)guanine, 8-chloro(bromo)guanosine, 8-chloro(bromo)adenine, 8-chloro(bromo)adenosine, 5-chloro(bromo)cytosine and 5-chloro(bromo)cytidine. Specific examples of the resulting selenonucleic acid base and selenoribosylnucleic acid base include 6-selenopurine, 6-selenopurineriboside, 6-selenoguanine, 6-selenoguanosine, 8-selenoguanine, 8-selenoguanosine, 8-selenoadenine, 8-selenoadenosine, 5-selenocytosine and 5-selenocytidine. A selenonucleic acid base or selenoribosylnucleic acid base is subsequently added to an aqueous solution containing about one mole of potassium tetrachloroplatinate (II) per mole of the selenonucleic acid base or selenoribosylnucleic acid base and about two moles of potassium hydroxide per mole of the selenonucleic acid base or selenoribosylnucleic acid base. Then, while stirring, the reaction is carried out at 0° to 80° C. for 1 to 24 hours to obtain a selenonucleic acid base dichloroplatinum (compound N), or a selenoribosylnucleic acid base dichloroplatinum (compound R) represented by the following formula:

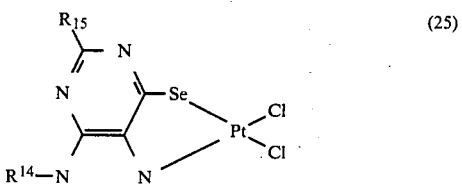

(wherein R$_{14}$ represents H for the compound N or a 1-β-D-ribofuranosyl group for the compound R and R$_{15}$ stands for H or an amino group);

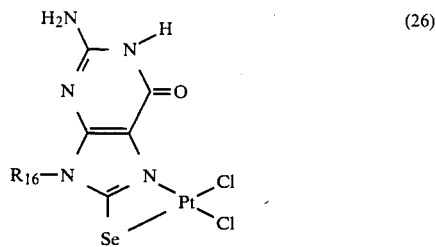

(wherein R$_{16}$ represents H for the compound N or a 1-β-D-ribofuranosyl group for the compound R);

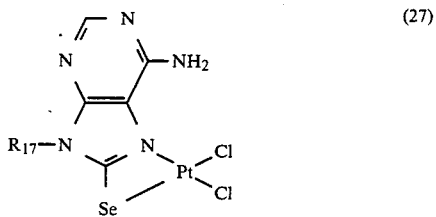

(wherein R$_{17}$ represents H for the compound N or a 1-β-D-ribofuranosyl group for the compound R); or

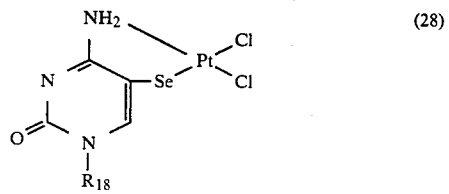

(wherein R$_{18}$ represents H for the compound N or a 1-β-D-ribofuranosyl group for the compound R).

Specific examples of the selenonucleic acid base dichloroplatinum and the selenoribosylnucleic acid base dichloroplatinum include 6-selenopurine dichloroplatinum, 6-selenopurineriboside dichloroplatinum, 6-selenoguanine dichloroplatinum, 6-selenoguanosine dichloroplatinum, 8-selenoguanine dichloroplatinum, 8-selenoguanosine dichloroplatinum, 8-selenoadenine dichloroplatinum, 8-selenoadenosine dichloroplatinum, 5-selenocytosine dichloroplatinum and 5-selenocytidine dichloroplatinum. The two chlorine atoms in the selenium-containing platinum compound thus obtained can be substituted with other substituents such as $NO_2$, $NO_3$, $>SO_3$, $>SO_4$ and

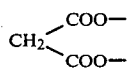

in substantially the same manner as described above with respect to the substitution of the two chlorine atoms of the selenoalkylamine dichloroplatinum represented by the formula (10) with other substituents such as $NO_2$, $NO_3$, $>SO_3$, $>SO_4$ and

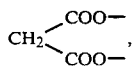

except that a selenonucleic acid base dichloroplatinum or selenoribosylnucleic acid base dichloroplatinum is used instead of a selenoalkylamine dichloroplatinum.

A selenium-containing platinum compound of the present invention represented by the formula (1) in which R and R' together stand for an unsubstituted or substituted selenosemicarbazide may be obtained as follows. For example, first, 4-phenylselenosemicarbazide as the unsubstituted or substituted selenosemicarbazide is synthesized according to K. A. Jensen et al, Z. Anorg. Allg. Chem., 230, 33(1936) and then, the obtained 4-phenylselenosemicarbazide is added to an aqueous solution containing about one mole of potassium tetrachloroplatinate (II) per mole of 4-phenylselenosemicarbazide and about two moles of potassium hydroxide per mole of 4-phenylselenosemicarbazide. Then, while stirring, the reaction is carried out at 0° to 80° C. for 1 to 24 hours to obtain 4-phenylselenosemicarbazide dichloroplatinum represented by the following formula:

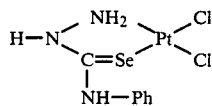

(Ph: phenyl group)

The two chlorine atoms of the thus obtained 4-phenylselenosemicarbazide dichloroplatinum can be substituted with other substituents such as $NO_2$, $NO_3$, $>SO_3$, $>SO_4$ and

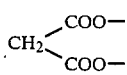

in substantially the same manner as described above with respect to the substitution of the two chlorine atoms of the selenoalkylamine dichloroplatinum represented by the formula (10) with other substituents such as $NO_2$, $NO_3$, $>SO_3$, $>SO_4$ and

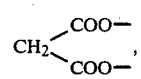

except that 4-phenylselenosemicarbazide dichloroplatinum is used instead of a selenoalkylamine dichloroplatinum.

X and X' in the formula (1) may together stand for phosphate, tartronate, hydroxymalonato, 1-dicarboxylate, phthalate, oxalate, tartrate, gluconate, succinato, glutarato, adipato, pimelato, malato or 4-carboxyphthalato, or X and X' in the formula (1) may each independently stand for pyruvate, cyanato or thiocyanato.

In a further aspect of the present invention, there is provided a method of prolonging the life of a patient suffering from cancer, which comprises administering to a patient an effective amount of the selenium-containing platinum compound of the formula (1) as defined above. The selenium-containing platinum compounds of the general formula (1) can be effectively used as a platinum compound type anti-cancer medicine which can self-detoxify platinum toxicity. These compoundds may be administered parenterally to human or animals, for example, in the form of an intravenous injection, an intramuscular injection, a hypodermical injection or an instillation after these compounds were dissolved or suspended in an appropriate solvent for injection such as a 5% aqueous glucose solution, a physiological saline, a distilled water for injection, an aqueous glycerol and an aqueous propylene glycol.

The selenium-containing platinum compounds of the present invention may be stored in an ampule in the form of a solution or suspension thereof. However, it is preferred that the selenium-containing platinum compounds of the present invention be stored in ampules or vials in the form of crystals, powders, fine crystals or freeze-dried material and an injectable solution be prepared just before the administration.

When the selenium-containing platinum compound of the present invention is used as an anti-cancer medicine, the dosage may vary depending upon ages, severities and body weights of patients, but a selenium-containing platinum compounds as an active ingredient may be usually administered in a daily dose of from about 1.0 to about 500 mg for adults, if necessary, in divided dosage forms.

The selenium-containing platinum compounds of the present invention can also be used as an antidote for platinum toxicity.

The following Examples illustrate the present invention in more detail but should not be construed as limiting the scope of the invention.

EXAMPLE 1

A number of experiments in which sodium selenite, sodium selenate, selenium yeast, selenocystine, amino acids containing selenium and proteins containing selenium were respectively given to mice both prior to and after treatment with platinum were conducted. In the first series of experiments in which these compounds were administered prior to the treatment with platinum, mice were given these materials in their drinking water over an extended period of time. Periodically, the mice were sacrificed and the kidney and liver were analyzed to monitor the accumulation of selenium. When observed selenium levels in the liver were no greater than 5 ppm, the remaining animals were given the platinum complexes at levels exceeding the reported $LD_{50}$ value. The platinum compounds that were tested included potassium platinum tetrachloride, Cisplatin and 4,5-dimethyl-o-phenylenediamine dichloro platinum (II). In the second series of experiments, in which the selenium compounds were administered after the platinum treatment, the mice were given dosages of the platinum compounds at levels above the reported $LD_{50}$ and were then injected with these materials. The selenium compounds were administered at times ranging from 1 hour to 3 days after the platinum injections. In both series of experiments, a control group which received platinum but no selenium compound was maintained. The result was that the mice which received this selenium treatment showed markedly reduced toxic effects from those which received only the platinum.

EXAMPLE 2

Male $BDF_1$ mice weighing about 25 g, each group consisting of 5 animals, were employed and Cisplatin was administered to the peritoneal cavities of the mice at a dosage of 14 mg/kg. Sodium selenite was administered to the peritoneal cavities of the mice at a dosage of 6.3 mg/kg. Then, the time of administration of sodium selenite was varied so that the administrations of sodium selenite to the respective groups of mice were conducted 4 hours before the administration of Cisplatin, 2 hours before the administration of Cisplatin, simultaneously with the administration of Cisplatin and 1 hour after the administration of Cisplatin. BUN of the mice was determined on the fourth day from the date of the administration. As control groups, there were maintained a group which did not receive both Cisplatin and sodium selenite, a group which received Cisplatin only and a group which received sodium selenite only. BUN of these control groups was also determined. The results are shown in Table 1.

TABLE 1

| Kinds of drugs and Dosage (mg/kg) | | Time when sodium selenite was administered | BUN on the fourth day (mg/kg) | |
|---|---|---|---|---|
| Sodium selenite | Cisplatin | | Average BUN*1 | BUN*2 ($\geq 30$) |
| 0 | 0 | — | 18 ± 2 | 0/5 |
| 6.3 | 0 | — | 18 ± 0.6 | 0/5 |
| 0 | 14 | — | 155 ± 7 | 4/5 |
| 6.3 | 14 | 4 hours before the administration of Cisplatin | 52 ± 21 | 4/5 |
| 6.3 | 14 | 2 hours before the administration of Cisplatin | 22 ± 9 | 1/3 (2)*3 |
| 6.3 | 14 | Simultaneously with the administration of Cisplatin | 44 ± 16 | 2/5 |
| 6.3 | 14 | 1 hour after the administration of Cisplatin | 133 ± 15 | 5/5 |

Note
*1 Average BUN value of mice which was determined on the fourth day from the date of administration of sodium selenite.
*2 The number of mice of which the BUN values each was 30 (mg/100 ml) or more on the fourth day from the date of administration of sodium selenite / Total number of mice is meant.
*3 The figure in parenthesis means the number of dead mice.

EXAMPLE 3

Male $BDF_1$ mice weighing about 25 g, each group consisting of 5 animals, were employed and Cisplatin was administered to the peritoneal cavities of the mice at a dosage of 14 mg/kg. Sodium selenite was administered to the peritoneal cavities of the mice at a dosage of 6.3 mg/kg. The time of administration of sodium selenite was varied so that the administrations of sodium selenite to the respective groups of mice were conducted 6 hours, 4 hours, 3 hours, 2 hours, and 1 hour before the administration of Cisplatin and simultaneously with the administration of Cisplatin. BUN of the mice was determined on the fourth day from the date of the administration. As control groups, there were maintained a group which did not receive both Cisplatin and sodium selenite and a group which received Cisplatin only. BUN of these control groups was also determined. The results are shown in Table 2.

TABLE 2

| Kinds of drugs and Dosage (mg/kg) | | Time when sodium selenite was administered | BUN on the fourth day (mg/kg) | |
|---|---|---|---|---|
| Sodium selenite | Cisplatin | | Average BUN*1 | BUN*2 ($\geq 30$) |
| 0 | 0 | — | 18 ± 3 | 1/5 |
| 0 | 14 | — | 111 ± 23 | 5/5 |
| 6.3 | 14 | 6 hours before the administration of Cisplatin | 48 ± 22 | 2/4(1)*3 |
| 6.3 | 14 | 4 hours before the administration of Cisplatin | 26 ± 5 | 2/4(1)*3 |
| 6.3 | 14 | 3 hours before the administration of Cisplatin | 31 ± 4 | 1/4(1)*3 |
| 6.3 | 14 | 2 hours before the administration of Cisplatin | 34 ± 16 | 1/5 |
| 6.3 | 14 | 1 hour before the administration of Cisplatin | 29 ± 7 | 3/5 |
| 6.3 | 14 | simultaneously with the administration of Cisplatin | 49 ± 17 | 2/4(1)*3 |

EXAMPLE 4

Male $BDF_1$ mice weighing about 25 g, each group consisting of 5 animals, were employed and Cisplatin was administered to the peritoneal caviteis of the mice at a dosage of 14 mg/kg. Predetermined amounts of sodium selenite were administered to the peritoneal cavities of the mice 2 hours before the administration of Cisplatin. BUN of the mice was dertermined on the fourth day from the date of administration and on the eleventh day from the date of the administration. As control groups, there were maintained a group which received Cisplatin only and a group which did not receive any drug. BUN of these control groups was also determined. The results are shown in Table 3.

TABLE 3

| Kinds of drugs and Dosage (mg/kg) | | BUN on the fourth day (mg/kg) | | BUN on the eleventh day (mg/kg) | |
|---|---|---|---|---|---|
| Sodium selenite | Cisplatin | Average BUN*1 | BUN*2 ($\geq 30$) | Average BUN*4 | BUN*5 ($\geq 30$) |
| — | — | 18 ± 2 | 0/5 | 19 ± 2 | 0/5 |
| — | 14 | 156 ± 25 | 5/5 | 52 ± 12 | 3/3(2)*2 |
| 8 | 14 | 27 ± 12 | 1/4(1)*3 | 21 ± 3 | 0/4(1)*3 |
| 6 | 14 | 51 ± 32 | 1/5 | 21 ± 2 | 0/4(1)*3 |
| 4 | 14 | 54 ± 33 | 1/4(1)*3 | 20 ± 3 | 0/3(2)*3 |
| 2 | 14 | 59 ± 36 | 1/5 | 20 ± 2 | 0/4(1)*3 |

TABLE 3-continued

| Kinds of drugs and Dosage (mg/kg) | | BUN on the fourth day (mg/kg) | | BUN on the eleventh day (mg/kg) | |
|---|---|---|---|---|---|
| Sodium selenite | Cisplatin | Average BUN[*1] | BUN[*2] ($\geq 30$) | Average BUN[*4] | BUN[*5] ($\geq 30$) |
| 1 | 14 | 39 ± 7 | 3/5 | 26 ± 4 | 1/5 |

Note
[*1], [*2] and [*3] See the Note of Table 1.
[*4] Average BUN value of mice which was determined on the eleventh day from the date of administration of sodium selenite.
[*5] The number of mice of which the BUN values each was 30 (mg/100 ml) or more on the eleventh day from the date of $\frac{\text{administration of sodium selenite}}{\text{Total number of mice}}$ is meant.

EXAMPLE 5

The purpose of this Example was to determine if the described selenium compounds could protect mice against Cisplatin induced nephrotoxicity as measured by blood urea nitrogen (BUN) determinations. Our studies were carried out in BDF$_1$ male mice weighing approximately 25 grams. All solutions were freshly were daily and given by the intraperitoneal route.

Using the maximum dose for each selenium compound given 2 hours prior to the injection of 14 mg/kg of Cis-platinol, a reduction of at least 30% or better was observed in all cases of the compounds listed below. The BUN values were determined on the fourth day after the administration of cisplatinol.

| LD$_{50}$ of Selenium Compounds | |
|---|---|
| Compound | LD$_{50}$ |
| sodium selenite | 3.25–3.50 mg Se/kg |
| sodium selenate | 5.25–5.75 mg Se/kg |
| selenocystine | 4.0 mg Se/kg |

EXAMPLE 6

Production of (HSeCH$_2$CH$_2$NH$_2$)$_2$PtCl$_2$

To 75 ml of 1M aqueous ethyleneimine solution was added 50 ml of 1M aqueous selenium hydride solution and the resulting mixture was stirred at room temperature for 24 hours. After completion of the reaction, the excess amount of ethyleneimine was removed by bubbling nitrogen gas through the solution. To the above obtained solution containing β-seleno ethylamine HSeCH$_2$CH$_2$NH$_2$ was added 10 mmol of potassium tetrachloroplatinate (II) and the resulting mixture was allowed to stand at room temperature for 2 days so that a precipitate was formed. The precipitate was separated by filtration and dried. Thus, the intended compound, (HSeCH$_2$CH$_2$NH$_2$)$_2$PtCl$_2$, was obtained.

Elementary analysis (%): Calculated: C; 9.34, H; 2.75, N; 5.45. Found: C; 9.38, H; 2.77, N; 5.41.

In the far infrared absorption spectrum, there were observed absorptions at 623 cm$^{-1}$ and 581 cm$^{-1}$ due to the Pt-N bond and absorptions at 335 cm$^{-1}$ and 320 cm$^{-1}$ due to the Pt-Cl bond.

EXAMPLE 7

Production of C$_6$H$_5$SeCH(CH$_2$NH$_2$)$_2$PtCl$_2$ 15 mmol of ClCH(COOC$_2$H$_5$)$_2$ and 10 mmol of C$_6$H$_5$SeNa were heated in 50 ml of ethanol under reflux for two hours. After completion of the reaction, the solvent was distilled off under reduced pressure to obtain C$_6$H$_5$SeCH(COOC$_2$H$_5$)$_2$. The thus obtained C$_6$H$_5$SeCH(COOC$_2$H$_5$)$_2$ was put in aqueous ammonia, and the reaction was allowed to proceed at 50° C. for 6 hours. After completion of the reaction, the solvent was distilled off under reduced pressure to obtain C$_6$H$_5$SeCH(CONH$_2$)$_2$. To the thus obtained C$_6$H$_5$SeCH(CONH$_2$)$_2$ were added 50 ml of tetrahydrofuran and then 2 mmol of lithium aluminum hydride. The resulting mixture was heated under reflux for 8 hours to reduce the amide. After completion of the reaction, the insoluble portion was removed and the solvent was distilled off under reduced pressure. Then, the residue was purified by column chromatography using silica gel as an adsorbent and chloroform-methanol (5:1) as a developing solvent to obtain 3 mmol of purified 2-phenylseleno-1,3-diaminopropane C$_6$H$_5$SeCH(CH$_2$NH$_2$)$_2$. To the thus obtained C$_6$H$_5$SeCH(CH$_2$NH$_2$)$_2$ was added 25 ml of an aqueous solution containing 3 mmol of potassium tetrachloroplatinate (II), and the resulting mixture was allowed to stand at room temperature for 3 days, so that C$_6$H$_5$SeCH(CH$_2$NH$_2$)$_2$PtCl$_2$ was obtained as a precipitate. The precipitate was separated by filtration and dried. There was obtained 1.2 mmol of the intended compound.

Elementary analysis (%): Calculated: C; 21.83, H; 2.86, N; 5.66. Found: C; 21.79, H; 2.88, N; 5.61.

In the far infrared spectrum, there were observed absorptions at 617 cm$^{-1}$ and 572 cm$^{-1}$ due to the Pt-N bond and absorptions at 330 cm$^{-1}$ and 322 cm$^{-1}$ due to the Pt-Cl bond.

EXAMPLE 8

Production of

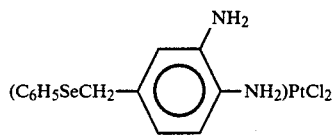

15 mmol of

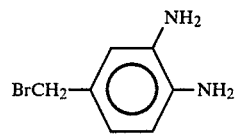

and 10 mmol of C$_6$H$_5$SeNa were heated in 50 ml of ethanol for 2 hours under reflux. After completion of the reaction, the solvent was distilled off under reduced pressure to obtain 4-phenylselenomethylene-1,2-diaminobenzene,

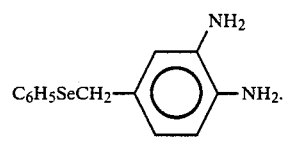

To the thus obtained

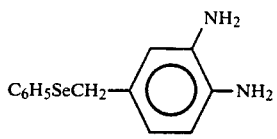

was added 100 ml of an aqueous solution containing 10 mmol of potassium tetrachloroplatinate(II) and the resulting mixture was allowed to stand at room temperature for 7 days, so that

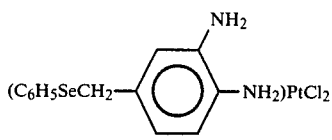

was obtained as a precipitate. The precipitate was separated by filtration and dried so that 4 mmol of the intended compound was obtained.

Elementary analysis (%): Calculated: C; 28.74, H; 2.60, N; 5.16. Found: C; 28.76, H; 2.57, N; 5.19.

In the far infrared spectrum, there were observed absorptions at 607 cm$^{-1}$ and 565 cm$^{-1}$ due to the Pt-N bond and absorptions at 324 cm$^{-1}$ and 314 cm$^{-1}$ due to the Pt-Cl bond.

EXAMPLE 9

Production of HSeCH(CH$_2$NH$_2$)$_2$PtCl$_2$ 15 mmol of ClCH(COOC$_2$H$_5$)$_2$ and 10 mmol of sodium selenide were heated in 50 ml of ethanol under reflux for 2 hours. After completion of the reaction, the reaction solution was slightly acidified with 1N HCl. Then, after insoluble material was removed from the solution, the reaction solvent was distilled off to obtain HSeCH(COOC$_2$H$_5$)$_2$. The thus obtained HSeCH-(COOC$_2$H$_5$)$_2$ was put in aqueous ammonia and the reaction was allowed to proceed at 50° C. for 6 hours. After completion of the reaction, the solvent was distilled off to obtain HSeCH(CONH$_2$)$_2$. To the thus obtained HSeCH(CONH$_2$)$_2$ were added 50 ml of tetrahydrofuran and then 2 mmol of lithium aluminum hydride. The resulting mixture was heated under reflux for 10 hours to reduce the amide. After completion of the reaction, the insoluble portion was removed and the solvent was distilled off under reduced pressure. Then, the residue was purified by using cation exchange resin to obtain 2 mmol of 2-seleno-1,3-diaminopropane HSeCH(CH$_2$NH$_2$)$_2$. To the thus obtained HSeCH(CH$_2$NH$_2$)$_2$ was added 20 ml of an aqueous solution containing 2 mmol of potassium tetrachloroplatinate (II) and the resulting mixture was allowed to stand at room temperature for 4 days, so that a precipitate was formed. The precipitate was separated by filtration and dried to obtain 1.1 mmol of HSeCH(CH$_2$NH$_2$)$_2$PtCl$_2$.

Elementary analysis (%): Calculated: C; 8.60 H; 2.41, N; 6.68. Found: C; 8.64, H; 2.39, N; 6.71.

In the far infrared spectrum, there were observed absorptions at 615 cm$^{-1}$ and 570 cm$^{-1}$ due to the Pt-N bond and absorptions at 326 cm$^{-1}$ and 321 cm$^{-1}$ due to the Pt-Cl bond.

EXAMPLE 10

Production of di-(selenomethionine)dichloroplatinum

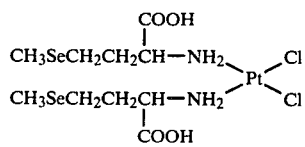

10 mmol of selenomethionine and 5 mmol of potassium tetrachloroplatinate (II) were added in 50 ml of warm water (40° C.) and stirred for 8 hours. The mixture was stirred subsequently at room temperature for 24 hours. After completion of the reaction, a precipitate formed was separated by filtration, washed with alcohol and next with acetone and dried to obtain 2.1 mmol of di-(selenomethionine)dichloroplatinum.

Elementary analysis (%): Calculated: C; 18.25, H; 3.37, N; 4.26. Found: C; 18.27, H; 3.34, N; 4.25.

In the far infrared spectrum, there were observed absorptions at 621 cm$^{-1}$ and 576 cm$^{-1}$ due to the Pt-N bond and absorptions at 332 cm$^{-1}$ and 317 cm$^{-1}$ due to the Pt-Cl bond.

EXAMPLE 11

Production of di-(selenohomomethionine)dichloroplatinum, di-(selenocysteine)dichloroplatinum, selenocystine dichloroplatinum and di-(methylselenocysteine)dichloroplatinum Di-(selenohomomethionine)dichloroplatinum, di-(selenocysteine)dichloroplatinum, selenocystine dichloroplatinum and di-(methylselenocysteine)dichloroplatinum were prepared in substantially the same manner as in Example 10 except that selenohomomethionine, selenocysteine, selenocystine and methylselenocysteine were respectively used instead of selenomethionine.

With respect to the compounds thus obtained, the result of the elementary analysis and the far infrared absorption spectrum are as follows.

[1] di-(selenohomomethionine)dichloroplatinum

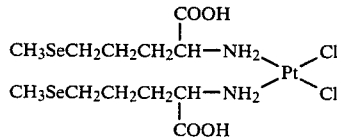

Elementary analysis (%): Calculated: C; 21.00, H; 3.79, N; 4.08. Found: C; 21.04, H; 3.83, N; 4.11.

In the far infrared spectrum, there were observed absorptions at 619 cm$^{-1}$ and 568 cm$^{-1}$ due to the Pt-N bond and absorptions at 328 cm$^{-1}$ and 321 cm$^{-1}$ due to the Pt-Cl bond.

[2] di-(selenocysteine)dichloroplatinum

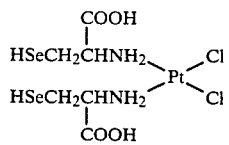

Elementary analysis (%): Calculated: C; 11.97, H; 2.34, N; 4.65. Found: C; 11.92, H; 2.38, N; 4.71.

In the far infrared spectrum, there were observed absorptions at 619 cm$^{-1}$ and 574 cm$^{-1}$ due to the Pt-N bond and absorptions at 331 cm$^{-1}$ and 316 cm$^{-1}$ due to the Pt-Cl bond.

[3] selenocystine dichloroplatinum

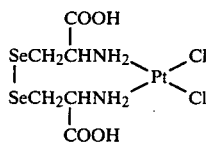

Elementary analysis (%): Calculated: C; 12.01, H; 2.02, N; 4.67. Found: C; 12.06, H; 2.05, N; 4.63.

In the far infrared spectrum, there were observed absorptions at 625 cm$^{-1}$ and 568 cm$^{-1}$ due to the Pt-N bond and absorptions at 329 cm$^{-1}$ and 320 cm$^{-1}$ due to the Pt-Cl bond.

[4] di-(methylselenocysteine)dichloroplatinum

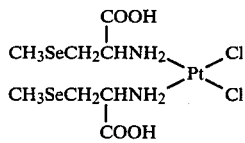

Elementary analysis (%): Calculated: C; 15.25, H; 2.88, N; 4.45. Found: C; 15.21, H; 2.91, N; 4.49.

In the far infrared spectrum, there were observed absorptions at 627 cm$^{-1}$ and 571 cm$^{-1}$ due to the Pt-N bond and absorptions at 325 cm$^{-1}$ and 316 cm$^{-1}$ due to the Pt-Cl bond.

EXAMPLE 12

Production of di-(2,3,4,6-tetra-O-acetyl-1-β-D-glucopyranosyl-seleno)dichloroplatinum

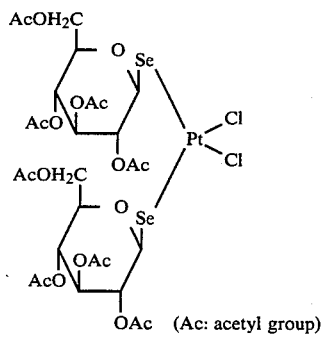

OAc  (Ac: acetyl group)

10.3 g of acetbromoglucose and 3.1 g of selenourea were added to 50 ml of acetone and the resulting mixture was refluxed to give (2,3,4,6-tetra-O-acetyl-1-β-D-glucopyranosyl)-2-selenoisoureahydrobromide. To a mixture of 3 ml of acetone, 7 ml of water and 110 mg (2 mmol) of potassium hydroxide were added 540 mg (1 mmol) of the above obtained compound, (2,3,4,6-tetra-O-acetyl-1-β-D-glucopyranosyl)-2-selenoisoureahydrobromide and 170 mg (0.5 mmol) of potassium tetrachloroplatinate (II). The resulting mixture was stirred at room temperature for 2 hours. After acetone was evaporated under reduced pressure, the precipitate formed was separated by filtration and dried to obtain 220 mg of the intended compound (Yield: 40%).

Elementary analysis (%): Calculated: C; 30.95, H; 3.53. Found: C; 30.87, H; 3.62.

In the far infrared absorption spectrum, there were observed absorptions at 325 cm$^{-1}$ and 318 cm$^{-1}$ due to the Pt-Cl bond.

Example 13

Production of di-(glucopyranosylseleno)dichloroplatinum

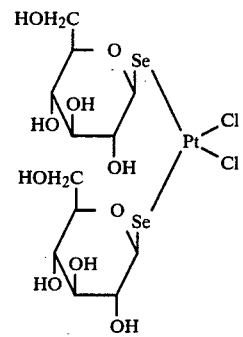

54 mg (1 mmol) of sodium methoxide and 330 mg (0.2 mmol) of di-(2,3,4,6-tetra-O-acetyl-1-β-D-glucopyranosylseleno)dichloroplatinum as prepared in the same manner as in Example 12 were added to 10 ml of absolute methanol and the resulting mixture was stirred at room temperature for 12 hours. After completion of the reaction, the reaction mixture was slightly acidified with 0.1N HCl, followed by addition of 5 ml of water. The remaining precipitate was separated by filtration and dried to obtain 120 mg of the intended compound.

Elementary analysis (%): Calculated: C; 19.21, H; 2.96. Found: C; 19.29, H; 2.91.

In the far infrared absorption spectrum, there were observed absorptions at 329 cm$^{-1}$ and 318 cm$^{-1}$ due to the Pt-Cl bond.

EXAMPLE 14

Production of Di-(2,3,4,6-tetra-O-acetyl-1-β-D-galactopyranosyl-seleno)dichloroplatinum

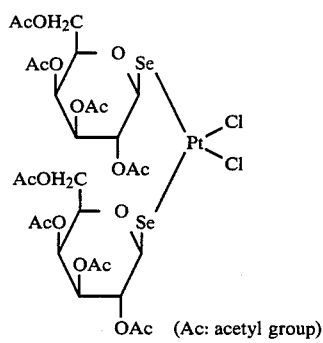

OAc  (Ac: acetyl group)

In substantially the same manner as described in Example 12, di-(2,3,4,6-tetra-O-acetyl-1-β-D-galactopyranosylseleno)dichloroplatinum was obtained except that acetbromogalactose was used instead of acetbromoglucose.

Elementary analysis (%): Calculated: C; 30.95, H; 3.53. Found: C; 30.88, H; 3.47.

In the far infrared absorption spectrum, there were observed absorptions at 332 cm$^{-1}$ and 316 cm$^{-1}$ due to the Pt-Cl bond.

EXAMPLE 15

Production of Di-(1-β-D-galactopyranosylseleno)dichloroplatinum

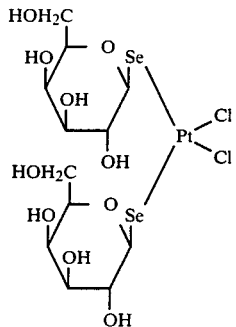

In substantially the same manner as described in Example 13, di-(1-β-D-glactopyranosylseleno)dichloroplatinum was obtained except that di-(2,3,4,6-tetra-O-acetyl-1-β-D-galactopyranosylseleno)dichloroplatinum as prepared in Example 14 was used instead of di-(2,3,4,6-tetra-O-acetyl-1-β-D-glucopyranosylseleno)dichloroplatinum.

Elementary analysis (%): Calculated: C; 19.21, H; 2.96. Found: C; 19.27, H; 3.01.

In the far infrared absorption spectrum, there were observed absorptions at 322 cm$^{-1}$ and 317 cm$^{-1}$ due to the Pt-Cl bond.

EXAMPLE 16

Production of Di-(2,3,4,6-tetra-O-acetyl-1-α-D-mannopyranosylseleno)dichloroplatinum

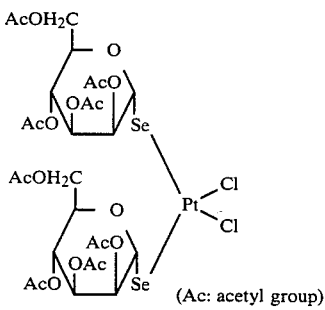

(Ac: acetyl group)

In substantially the same manner as described in Example 12, di-(2,3,4,6-tetra-O-acetyl-1-α-D-mannopyranosylseleno)dichloroplatinum was obtained except that acetbromomannose was used instead of acetbromoglucose.

Elementary analysis (%): Calculated: C; 30.95, H; 3.53. Found: C; 31.01, H; 3.48.

In the far infrared absorption spectrum, there were observed absorptions at 334 cm$^{-1}$ and 321 cm$^{-1}$ due to the Pt-Cl bond.

EXAMPLE 17

Production of Di-(1-α-D-mannopyranosylseleno)dichloroplatinum

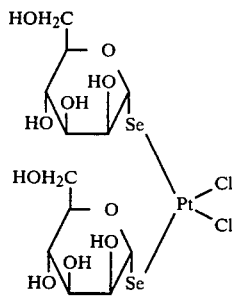

In substantially the same manner as described as in Example 13, di-(1-α-D-galactopyranosylseleno)dichloroplatinum was obtained except that di-(2,3,4,6-tetra-O-acetyl-1-α-D-mannopyranosylseleno)dichloroplatinum was used instead of di-(2,3,4,6-tetra-O-acetyl-1-β-D-glucopyranosylseleno)dichloroplatinum.

Elementary analysis (%): Calculated: C; 19.21, H; 2.96. Found: C; 19.13, H; 3.02.

In the far infrared absorption spectrum, there were observed absorptions at 327 cm$^{-1}$ and 319 cm$^{-1}$ due to the Pt-Cl bond.

EXAMPLE 18

Production of 6-selenoguanine dichloroplatinum

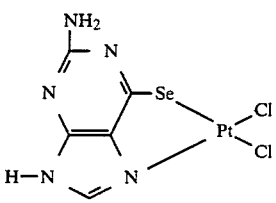

1.7 g (10 mmol) of 6-chloroguanine and 1.2 g (10 mmol) of selenourea were put in 30 ml of absolute ethanol and boiled under reflux for 2 hours. After completion of the reaction, the resulting precipitate was separated by filtration, washed with water and dissolved in 200 ml of 2 wt% aqueous sodium carbonate solution by heating. The resulting solution was acidified with acetic acid to form crystals. The crystals were separated by filtration and dried to obtain 1.5 g (7 mmol) of 6-selenoguanine.

1.0 g (5 mmol) of 6-selenoquanine thus obtained was added to 30 ml of an aqueous solution containing 1.7 g (5 mmol) of potassium tetrahchloroplatinate (II) and 560 mg (10 mmol) of potassium hydroxide and stirred at room temperature for 10 hours. The resulting precipitate was separated by filtration and dried to obtain 1.4 g (3 mmol) of 6-selenoguanine dichloroplatinum.

Elementary analysis (%): Calculated: C; 12.53, H; 0.84, N; 14.62. Found: C; 12.41, H; 0.89, N; 14.67.

In the far infrared absorption spectrum, there were observed absorptions at 328 cm$^{-1}$ and 318 cm$^{-1}$ due to the Pt-Cl bond.

EXAMPLE 19

Production of 6-selenoguanosine dichloroplatinum

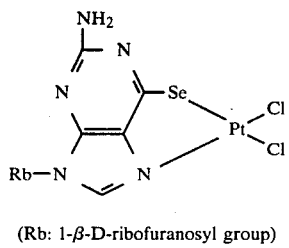

(Rb: 1-β-D-ribofuranosyl group)

0.16 g of sodium was added to 15 ml of absolute ethanol and the resulting mixture was saturated with hydrodiene selenide while cooling with ice. In a nitrogen atmosphere, the reaction was allowed to proceed for 6 hours. Then, 0.98 mg of 6-chloroguanosine and 20 ml of ethanol was added to the reaction mixture and boiled under reflux for 18 hours. After completion of the reaction, 30 ml of water was added to the reaction mixture and the insoluble substances were removed by filtration. The filtrate was cooled with ice and acidified with 3 ml of acetic acid. The resulting precipitate was separated by filtration and dried to give 700 mg of 6-selenoguanosine.

520 mg of 6-selenoguanosine thus obtained was added to 15 ml of an aqueous solution containing 500 mg of potassium tetrachloroplatinate (II) and 84 mg of potassium hydroxide and stirred for 8 hours. The resulting precipitate was separated by filtration and dried to give 600 mg of 6-selenoguanosine dichloroplatinum.

Elementary analysis (%): Calculated: C; 19.65, H; 1.98, N; 11.46. Found: C; 19.72, H; 1.87 N; 11.52.

In the far infrared absorption spectrum, there were observed absorptions at 325 cm$^{-1}$ and 318 cm$^{-1}$ due to the Pt-Cl bond.

EXAMPLE 20

Production of 5-selenocytosine dichloroplatinum

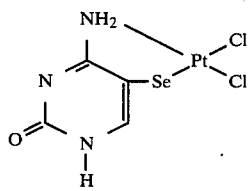

1.9 g of 5-bromocytosine and 1.2 g of selenourea were added to 30 ml of absolute ethanol and the resulting mixture was boiled under reflux for 2 hours. After completion of the reaction, the resulting precipitate was separated by filtration, washed with water and dissolved in 200 ml of 2 wt% aqueous sodium carbonate by heating. The resulting solution was acidified with acetic acid to form crystals. The crystals were separated by filtration and dried to give 1.2 g of 5-selenocytosine.

950 mg of 5-selenocytosine thus obtained was added to 30 ml of an aqueous solution containing 1.7 g of potassium tetrachloroplatinate (II) and 560 mg of potassium hydroxide and stirred at room temperature for 10 hours. The resulting precipitate was separated by filtration and dried to obtain 1.1 g of 5-selenocytosine dichloroplatinum.

Elementary analysis (%): Calculated: C; 10.58, H; 0.67, N; 9.26. Found: C; 10.71, H; 0.73, N; 9.22.

In the far infrared absorption spectrum, there were observed absorptions at 330 cm$^{-1}$ and 318 cm$^{-1}$ due to the Pt-Cl bond.

EXAMPLE 21

Production of 5-selenocytidine dichloroplatinum

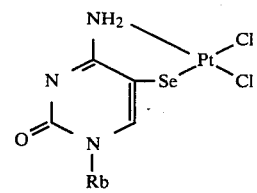

(Rb: 1-β-D-ribofuranosyl group)

3.22 g of 5-bromocytidine and 1.2 g of selenourea were added to 30 ml of absolute ethanol and the resulting mixture was boiled under reflux for 2 hours. After completion of the reaction, the resulting precipitate was separated by filtration, washed with water and dissolved in 200 ml of 2 wt% aqueous sodium carbonate by heating. The resulting solution was then acidified with acetic acid to give crystals. The crystals thus obtained were separated by filtration and dried to obtain 1.9 g of 5-selenocytidine.

1.6 g of 5-selenocytidine thus obtained was added to 30 ml of an aqueous solution containing 1.7 g of potassium tetrachloroplatinate (II) and 560 mg of potassium hydroxide and stirred at room temperature for 10 hours to form a precipitate. The resulting precipitate was separated by filtration and dried to obtain 1.2 g of 5-selenocytidine dichloroplatinum.

Elementary analysis (%): Calculated: C; 18.44, H; 1.89, N; 7.17. Found: C; 18.52, H; 1.77. N; 7.23.

In the far infrared absorption spectrum, there were observed absorptions at 324 cm$^{-1}$ and 316 cm$^{-1}$ due to the Pt-Cl bond.

EXAMPLE 22

Production of 4-phenylselenosemicarbazide dichloroplatinum

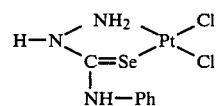

(Ph: phenyl group)

1.1 g of 4-phenylselenosemicarbazide was added to 30 ml of an aqueous solution containing 1.7 g of potassium tetrachloroplatinate (II) and 560 mg of potassium hydroxide and stirred at room temperature for 10 hours. The resulting precipitate was separated by filtration and dried to obtain 1.2 g of 4-phenylselenosemicarbazide dichloroplatinum.

Elementary analysis (%): Calculated: C; 17.51, H; 1.89, N; 8.75. Found: C; 17.64, H; 1.81, N; 8.72.

In the far infrared absorption spectrum, there were observed absorptions at 328 cm$^{-1}$ and 318 cm$^{-1}$ due to the Pt-Cl bond.

EXAMPLE 23

6-selenopurine dichloroplatinum and 6-selenopurineriboside dichloroplatinum were prepared in substantially the same manner as described in Example 18 except that 6-chloropurine and 6-chloropurineriboside were respectively used instead of 6-chloroguanine.

[1] 6-selenopurine dichloroplatinum

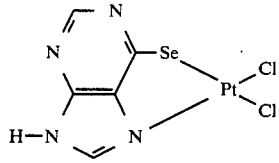

Elementary analysis (%): Calculated: C; 13.34, H; 0.67, N; 9,34. Found: C; 13.41, H; 0.62, N; 9.28.

In the far infrared absorption spectrum, there were observed absorptions at 333 cm$^{-1}$ and 318 cm$^{-1}$ due to the Pt-Cl bond.

[2] 6-selenopurineriboside dichloroplatinum

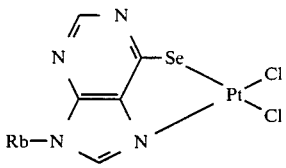

(Rb: 1-β-D-ribofuranosyl group)

Elementary analysis (%): Calculated: C; 20.63, H; 1.90, N; 7.22. Found: C; 20.54, H; 1.97, N; 7.16.

In the far infrared absorption spectrum, there were observed absorptions at 325 cm$^{-1}$ and 318 cm$^{-1}$ due to the Pt-Cl bond.

EXAMPLE 24

8-Selenoguanine dichloroplatinum, 8-selenoguanosine dichloroplatinum, 8-selenoadenine dichloroplatinum and 8-selenodenosine dichloroplatinum were prepared in substantially the same manner as described in Example 20 except that 8-bromoguanine, 8-bromoguanosine, 8-bromoadenine and 8-bromoadenosine were respectively used instead of 5-bromocytosine.

[1] 8-Selenoguanine dichloroplatinum

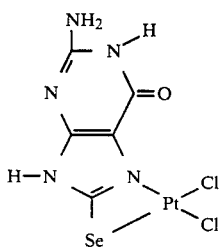

Elementary analysis (%); Calculated: C; 13.93, H; 0.94, N; 16.25. Found: C; 14.01, H; 0.87, N; 16.19.

In the far infrared absorption spectrum, there were observed absorptions at 335 cm$^{-1}$ and 320 cm$^{-1}$ due to the Pt-Cl bond.

[2] 8-Selenoguanosine dichloroplatinum

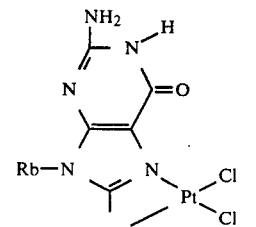

(Rb: 1-β-D-ribofuranosyl group)

Elementary analysis (%): Calculated: C; 19.15, H; 1.93, N; 11.17. Found: C; 19.21, H; 1.87, N; 11.22.

In the far infrared absorption spectrum, there were observed absorptions at 335 cm$^{-1}$ and 320 cm$^{-1}$ due to the Pt-Cl bond.

[3] 8-Selenoadenine dichloroplatinum

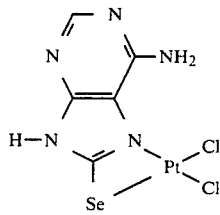

Elementary analysis (%): Calculated: C; 13.93, H; 0.94, N; 16.25. Found: C; 13.88, H; 1.01, N; 16.19.

In the far infrared absorption spectrum, there were observed absorptions at 332 cm$^{-1}$ and 318 cm$^{-1}$ due to the Pt-Cl bond.

[4] 8-Selenoadenosine dichloroplatinum

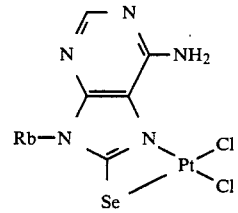

(Rb: 1-β-D-ribofuranosyl group)

Elementary analysis (%); Calculated: C; 19.68, H; 1.82, N; 11.48. Found: C; 19.72, H; 1.87, N; 11.53.

In the far infrared absorption spectrum, there were observed absorptions at 330 cm$^{-1}$ and 322 cm$^{-1}$ due to the Pt-Cl bond.

What is claimed is:

1. A method of negating the toxic effects of platinum compounds, which comprises administering to a patient having a problem due to undergoing platinum therapy an effective amount of at least one selenium-containing compound selected from the group consisting of sodium selenite, sodium selenate, selenium yeast, an amino acid containing selenium, an amine containing selenium, a seleno carbohydrate and a seleno heterocyclic base, said amino acid containing selenium being at least one member selected from the group consisting of selenomethionine, selenocysteine, Se-methylselenocysteine, selenohomomethionine, selenohomocystine and selenocystine, said amine containing selenium being at least one member selected from the group consisting of β-seleno ethylamine, 2-phenylseleno-1,3-diaminopropane, 4-phenylselenomethylene-1,2-diaminobenzene, 2-seleno-1,3-diaminopropane and 4-phenylselenosemicarbazide, said seleno carbohydrate being at least one member selected from the group consisting of 1-β-D-seleno-2,3,4,6-tetra-O-acetyl-D-glucopyranose, selenoglucopyranose, 1-β-D-seleno-2,3,4,6-tetra-O-acetyl-D-galactopyranose, 1-β-D-selenogalactopyranose, 1-α-D-seleno-2,3,4,6-tetra-O-acetyl-D-mannopyranose and 1-α-D-selenomannopyranose, said seleno heterocyclic base being at least one member selected from the group consisting of 6-selenoguanine, 6-selenoguanosine, 5-selenocytosine, 5-selenocytidine, 6-selenopurine, 6-selenopurineriboside, 8-selenoguanine, 8-selenoguanosine, 8-selenoadenine and 8-selenoadenosine.

2. A method according to claim 1, wherein said effective amount of a selenium-containing compound is about 0.6 to 300 mg for adults per day.

* * * * *

UNITED STATES PATENT AND TRADEMARK OFFICE
CERTIFICATE OF CORRECTION

PATENT NO. : 4,617,189
DATED : October 14, 1986
INVENTOR(S) : RICHARD F. STOCKEL ET AL It is certified that error appears in the above-identified patent and that said Letters Patent is hereby corrected as shown below:

On the cover page, Item [60], change "Jan. 16, 1984" to --- October 16, 1981 ---.

Signed and Sealed this

Twenty-eighth Day of April, 1987

Attest:

DONALD J. QUIGG

*Attesting Officer*   *Commissioner of Patents and Trademarks*